US007989411B2

(12) United States Patent
Pey Gutiérrez et al.

(10) Patent No.: US 7,989,411 B2
(45) Date of Patent: Aug. 2, 2011

(54) COMPOSITION WHICH CONTAINS A MIXTURE OF MONO-, DI AND TRIGLYCERIDES AND GLYCERINE

(75) Inventors: Carmen Ma Pey Gutiérrez, Barcelona (ES); Blanca Nogués López, Barcelona (ES); Maria José Bermejo Osés, Barcelona (ES); Hiroshi Abe, Barcelona (ES)

(73) Assignee: Kao Corporation, S.A., Barcelona (ES)

(*) Notice: Subject to any disclaimer, the term of this patent is extended or adjusted under 35 U.S.C. 154(b) by 94 days.

(21) Appl. No.: 12/226,715

(22) PCT Filed: Apr. 3, 2007

(86) PCT No.: PCT/EP2007/053271

§ 371 (c)(1),
(2), (4) Date: Jul. 14, 2009

(87) PCT Pub. No.: WO2007/141066

PCT Pub. Date: Dec. 13, 2007

(65) Prior Publication Data

US 2010/0035781 A1 Feb. 11, 2010

(30) Foreign Application Priority Data

Jun. 7, 2006 (ES) .................................. 200601535

(51) Int. Cl.

| | |
|---|---|
| ***C11D 1/722*** | (2006.01) |
| ***C11D 1/74*** | (2006.01) |
| ***C11D 1/825*** | (2006.01) |
| ***C11D 11/04*** | (2006.01) |
| ***A61K 8/37*** | (2006.01) |

(52) U.S. Cl. ........ 510/437; 510/506; 554/161; 554/163; 554/227

(58) Field of Classification Search .................. 510/437, 510/506; 554/161, 163, 227
See application file for complete search history.

(56) References Cited

U.S. PATENT DOCUMENTS 5,403,509 A * 4/1995 Pujol et al. .................... 510/535

FOREIGN PATENT DOCUMENTS

EP 31045021 A1 10/2000
EP 21106675 6/2001

OTHER PUBLICATIONS

Informe de Estado de la Tecnica (IET) issued by the Spanish Patent and Trademark Office in connection with the patent application ES P200601535 whose priority date is invoked by the subject application, Mar. 7, 2008.

International Search Report issued by the International Searching Authority (ISA/EP) on Jul. 20, 2007 in connection with International Application No. PCT/EP2007/053271.

International Preliminary Report on Patentability issued by the International Searching Authority (ISA/EP) in connection with International Application No. PCT/EP2007/053271, Jun. 25, 2008.

Nov. 10, 2010 Opposition, Evonik Goldschnidt GmbH 45116 Essen, Germany, European Patent 2 029 711 B1, application No. 07727742.4.

PCT International Application Publication No. WO 00/47315 (Cognis Deutschland GMBH DE/DE) published Aug. 17, 2000, Exhibit to Opposition D1 [Exhibit 1].

European Patent Application No. 0 702 079 A2, (Kao Corporation), Mar. 20, 1996 Exhibit to Opposition D2 [Exhibit 1].

European Patent Application No. 1 045 021, (Kao Corporation, S.A. ), Oct. 18, 2000 Exhibit to Opposition D3 [Exhibit 1].

European Patent Application No. 0 586 323 A1, (Kao Corporation, S.A. ), Mar. 9, 1994 Exhibit to Opposition D4 [Exhibit 1].

European Patent Application No. 1 106 675 A2, (Cognis Deutschland GmbH) , Jun. 13, 2001 Exhibit to Opposition D5 [Exhibit 1].

Condon, Brian D., Foam Enhancement by Short-Chain Hydrophobe Alcohol Ethoxylates in Light-Duty Liquids, JAOCS, vol. 71, No. 7 (Jul. 1994), pp. 783-787 Exhibit to Opposition D6 [Exhibit 1].

Kokosfett, ROMPP, Online, version 3.8 Exhibit to Opposition D7 [Exhibit 1], 2010.

NMR spectrum of an ethoxylated glyceride/glycerol mixture Exhibit to Opposition D8 [Exhibit 1].

* cited by examiner

*Primary Examiner* — Brian P Mruk
(74) *Attorney, Agent, or Firm* — Gary J. Gershik; Cooper & Dunham LLP

(57) ABSTRACT

The present invention relates to a composition which contains a mixture of alkoxylated mono-, di-, and triglycerides and glycerine of formula wherein R' represents H or CH3, and each one of m, n, or l represents, independently, a number from 0 to 20, the sum of m, n, and l being in the range of 1.5 to 20, characterized in that in the acyl group represented by —CO—R, R represents an alkyl or alkenyl group, linear or branched, of 6 to 11 carbon atoms, and the proportion by weight (i)+(ii)+(iii)/(iv) is in the range of 2.0:0.5 to 0.5:3; and to a method for the preparation of said composition, the detergent compositions which contain said compositions, and the use of said composition as surfactant or co-surfactant in the detergent compositions, particularly in detergent compositions, especially, but not exclusively, suitable for washing fabrics, suitable for manual dishwashing, for washing the hair or for personal hygiene.

(1)

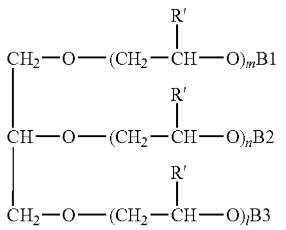

18 Claims, No Drawings

COMPOSITION WHICH CONTAINS A MIXTURE OF MONO-, DI AND TRIGLYCERIDES AND GLYCERINE

This application is a §371 national stage of PCT International Application No. PCT/EP2007/053271, filed Apr. 3, 2007, and claims priority of Spanish Patent Application No. P200601535, filed Jun. 7, 2006, the contents of all of which are hereby incorporated by reference into this application.

FIELD OF THE INVENTION

The present invention relates to a composition which contains a mixture of alkoxylated mono-, di-, and triglycerides and glycerine, to a method for the preparation of said composition, the detergent compositions which contain said composition and to the use of said composition as surfactant or co-surfactant in detergent compositions, particularly in detergent compositions, especially, but not exclusively, suitable for washing fabrics, suitable for manual dishwashing, for washing the hair or for personal hygiene.

PRIOR ART

Most of the known detergent compounds use surfactants of anionic, amphoteric and/or non-ionic type to produce a final product which displays satisfactory properties in terms of detergence and foam profile. However, most of these compounds are not generally satisfactory due to the problem of ecotoxicity and irritation to the eyes and skin.

On the other hand, in a large number of applications where surfactants are used, consumers look for a large quantity of foam to be produced. For example, a shampoo that does not produce stable, creamy foam during the washing process is expected not to be well accepted in the market. The same applies to manual dishwashing, even when a direct relation cannot be formed between the foaming power and cleaning efficacy.

The main characteristics of the surfactant formulations related to foam which determine their use in areas such as personal hygiene and domestic cleaning, the food sector, fire-fighting, mineral flotation and many others are: foaming capability, foam stability (the foam remaining after a period of time), foam quantity (associated to a good cleaning effect), the creaminess of the foam (associated to conditioning effect), foam density, foam texture and speed of foaming (foam produced after a very short period of time). On the other hand, it is desirable that the foam is quickly produced (e.g. after a few seconds). Furthermore, the foam must tolerate hard water and the presence of oil and/or greases.

The number of combinations of surfactants which solve this complex requirement tends to be reduced, which explains why the same formulations are always on the market. One way of overcoming this problem would be to incorporate additives known as foaming amplifiers or re-enforcers.

On the other hand, the compositions which contain a mixture of alkoxylated mono-, di-, and triglycerides and glycerine are well known by persons skilled in the art.

Thus, patent application EP-A-0586323 discloses a detergent composition which displays improved properties with respect to ecotoxicity and irritation to the eyes and skin; said composition comprises the mono-, di- and triester compounds represented by formula (I), wherein the proportion by weight of mono-, di-, and triester is 46-90/9-30/1-15

(I)

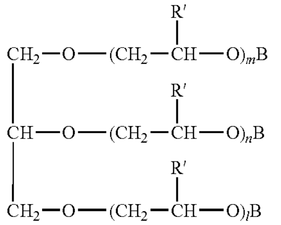

wherein R' represents H or $CH_3$, B represents H or the group represented by —CO—R, with the condition that R represents an alkyl or alkenyl group with $C_6$-$C_{22}$, and each one of n, m and l independently represent a whole number between 0 and 40; with n+m+l=2-100, preferably 9-19, and the compound represented by formula (II)

(II)

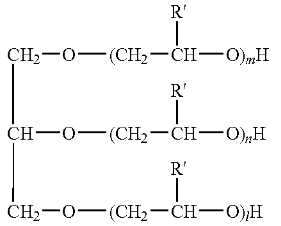

wherein each one of n, m and l independently represent a whole number between 0 and 40; with n+m+l=2-100, preferably 9-19, wherein the proportion by weight (I)/(II) has a value between 3 and 0.33 (3:1 and 1:3), preferably between 1.3 and 0.75 (3:2.3 and 2.25:3)

On the other hand, patent application EP-A-1045021 discloses a composition which displays high viscosity and good foam stability, as well as good properties with respect to biodegradability and irritation to the eyes and skin, said composition comprises (i) components represented by formula (III), wherein, independently, each one of the symbols B1, B2 and B3 represents an acyl group represented by —CO—R (ii) components represented by formula (III), wherein, independently, two of the symbols B1, B2 and B3 represent an acyl group represented by —CO—R and the remaining ones represent H;

(iii) components represented by formula (III), wherein, independently, one of the symbols B1, B2, B3 represents an acyl group represented by —CO—R and the remaining ones represent H;

(iv) components represented by formula (III), wherein each one of B1, B2 and B3 represents H; with the proportion by weight of components (iii)/(ii)/(i) (proportion by weight of mono-, di-, and triester) 46-90/9-35/1-15, preferably of 60-83/16-35/1-6, (III)

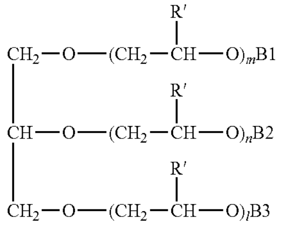

wherein R' represents H or $CH_3$, and each one of m, n, or l represents, independently, a number from 0 to 4, the sum of m, n and l being in the range of 1 to 4, preferably in the range of 1 to a number less than 2, even more preferably from 1.5 to a number lower than 2, and in the acyl group represented by —CO—R, R represents an alkyl or alkenyl group of 6 to 22 carbon atoms, the proportion by weight (iii)+(ii)+(i)/(iv) being in the range of 85/15 to 40/60 (5.67:1 to 1:1.5), preferably from 80/20 to 45/55 (4:1 to 1:1.2).

Finally, patent application EP-A-1106675 discloses the use of ethoxylated partial glyceride products which consist of mixtures of ethoxylated partial glycerides of formula (IV)

(IV)

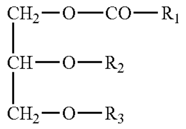

wherein —CO—$R_1$ represents an acyl group of 6 to 22 carbon atoms, linear or branched, saturated or unsaturated, and $R_2$ and $R_3$ represent, independently from one another, hydrogen or —CO—$R_1$, with the condition that either $R_2$ or $R_3$ is hydrogen, and ethoxylated glycerol in a proportion by weight in the range of 6:1 to 3.3:1 for the production of detergents for washing fabrics, detergents for dishwashing and cleaners, especially in the form of detergent tablets. In accordance with EP-A-1106675, the proportion by weight of mono-, di-, and triester is 46-90/9-30/1-15, and the products which are used (mixtures of ethoxylated partial glycerides of formula (IV) and ethoxylated glycerol) are addition products of 1 to 50 moles of ethylene oxide per mole of partial glyceride, preferably from 5 to 20 moles of ethylene oxide.

Despite the fact that the compositions disclosed in EP-A-0586323, EP-A-1045021 and EP-A-1106675 have a certain foaming power, in certain cases, greater foaming is required. Therefore, in some cases, said compositions have been combined with other surfactants, such as, for example, ether carboxylic acids or their salts, as disclosed in patent application WO-A-2004104150. Nevertheless, said combination is not always possible depending on the field of application, especially when there are cationic surfactants in the medium, which may interact with the ether carboxylic acids or their salts. On the other hand, it is more versatile to have a single compound (composition in this case) which has all the above described advantages and, at the same time, is capable of producing a high quantity of foam without having to be combined with other compounds.

DESCRIPTION OF THE INVENTION

The present invention provides an effective solution to the problems mentioned in the state of the art, providing a composition which comprises (i) at least one component represented by formula (1), wherein, independently, one of the symbols B1, B2, B3 represents an acyl group represented by —CO—R and the remaining ones represent H (ii) at least one component represented by formula (1), wherein, independently, two of the symbols B1, B2 and B3 represent an acyl group represented by —CO—R and the remaining one represents H;

(iii) at least one component represented by formula (1), wherein, independently, each one of the symbols B1, B2 and B3 represents an acyl group represented by —CO—R;

(iv) at least one component represented by formula (1), wherein each one of B1, B2 and B3 represents H (1)

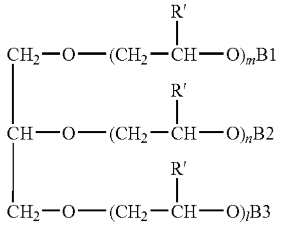

with the proportion by weight of components (i)/(ii)/(iii) of 60-90/10-35/less than 10, in the formula (1) R' represents H or $CH_3$, each one of m, n, or l represents, independently, a number of 0 to 20, the sum of m, n and l being in the range of 1.5 to 20, characterized in that in the acyl group represented by —CO—R, R represents an alkyl or alkenyl group, linear or branched, with 6 to 11 carbon atoms, and the proportion by weight (i)+(ii)+(iii)/(iv) is in the range of 2.0:0.5 to 0.5:3.0.

The methods for preparing said composition also form part of the object of the invention.

Another additional object of the present invention are the detergent compositions which contain said composition.

The use of said composition as surfactant or co-surfactant in detergent compositions also forms part of the object of the invention.

The use of said composition as amplifying or promoting agent of foaming in detergent compositions also forms part of the object of the invention.

DETAILED DESCRIPTION OF THE INVENTION

The composition of the invention contains a mixture of alkoxylated mono-, di-, and triglycerides and glycerine.

Preferably, the proportion by weight of components (i)/(ii)/(iii) is 80-90/10-25/less than 6.

Preferably, in formula (1) R' represents H, i.e. components (i), (ii), (iii) and (iv) are ethoxylated derivates.

Preferably, the sum of m, n and l is in the ranges of 2 to 15, even more preferably in the range over 5 and less than 9.

Preferably, the proportion by weight (i)+(ii)+(iii)/(iv) is in the range of 1.5:0.8 to 0.8:2.5, more preferred in the range of 1.3:0.9 to 0.9:2.3, even more preferred in the range of 1.2:1.0 to 1.0:2.0.

Preparation Method

The compositions of the present invention can be prepared as described in patent application EP-A-1045021, i.e. by a first method that consists of the following stages:

a) a mixture of glycerine and a component of formula (2) is subjected to an interesterification reaction: wherein R represents an alkyl or alkenyl group, linear or branched, of 6 to 11 carbon atoms, (2)

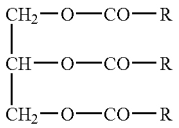

and b) the reaction mixture produced in stage a) is subjected to an alkoxylation using an alkylene oxide with 2 or 3 carbon atoms in the presence of an alkaline catalyst.

The interesterification reaction of stage a) is governed by thermodynamics. Consequently, the molar proportion of components (i), (ii), (iii) and (iv) in the final product is determined by the proportion of starting materials, glycerine and the component of formula (2). The subsequent alkoxylation reaction of stage b) is a reaction which generally proceeds quantitatively, whereby the quantity of alkylene oxide used determines the degree of alkoxylation (i.e. the sum of m, n, and l). The molar proportion of components (i), (ii), (iii) and (iv) is not affected by alkoxylation, since the alkylene oxide only reacts with the free moieties of the hydroxyl groups of the mono- and diester and glycerine molecules. However, the proportion by weight of components (i), (ii), (iii) and (iv), consequently, changes. Despite the fact that the result of the reactions of stages a) and b) can be predicted by a person skilled in the art, it is possible to use model calculations to determine the correct proportion of the starting materials and thus obtain a proportion of predetermined and specific weights of components (i), (ii), (iii), and (iv) and a predetermined and specific degree of alkoxylation.

Furthermore, the compositions of the present invention can be produced by a second method which consists of the following stages:

a') a mixture of glycerine is made to react with alkylene oxide with 2 or 3 carbon .atoms in the presence of an alkaline catalyst, and b') the reaction mixture produced in stage a') is made to react with a component of formula (3)

$$R—CO—OX \quad (3)$$

wherein R represent an alkyl or alkenyl group, linear or branched, of 6 to 11 carbon atoms and X represents a methyl group or H.

The component of formula (2) includes vegetable and animal oils and fats, as well as synthetic triglycerides, produced from esterification of fatty acids $C_6$-$C_{12}$ and glycerine.

Examples of fatty acids of general formula (3) or of their methyl esters which are condensed (transesterify) with a mixture of glycerine with alkylene oxide with 2 or 3 carbon atoms are fatty acids $C_6$-$C_{12}$ from vegetable and animal oils and fats, possibly totally or partially hydrogenated, as well as purified or synthetic fatty acids such as caproic acid ($CH_3$ $(CH_2)_4$ COOH), enanthic acid ($CH_3(CH_2)_5COOH$), caprylic acid ($CH_3(CH_2)_6COOH$), pelargonic acid ($CH_3(CH_2)_7COOH$), capric acid ($CH_3(CH_2)_8COOH$), 2-ethyl caproic acid or 2-ethylhexanoic acid ($CH_3(CH_2)_3CH(C_2H_5)COOH$), undecylic acid ($CH_3(CH_2)_9COOH$), lauric acid ($CH_3(CH_2)_{10}$ COOH) or mixtures thereof.

Preferably, the fatty acids of general formula (3) their methyl esters, or the fatty acids that are esterified with glycerine to produce the component of formula (2), are selected from caproic acid, enanthic acid, caprylic acid, pelargonic acid, capric acid, 2-ethyl caproic acid, or mixtures thereof.

Preferably, the content of $C_{11}$ in the acyl group represented by —CO—R of formula (1) is equal to or less than 5% by weight, even more preferably equal to or less than 2% by weight.

It is particularly preferred that in the acyl group represented by —CO—R of formula (1), R represents an alkyl or alkenyl group, linear or branched, of 6 to 9 carbon atoms.

The degree of alkoxylation of the final product (i.e. the sum of m, n, and l) is determined by the quantity of alkylene oxide used in stage a'). Next, stage b) determines the molar proportion and the proportion by weight of components (i), (ii), (iii), and (iv). As before, the result of the reactions of stages a') and b') can be predicted by a person skilled in the art, so that it is possible to use model calculations to determine the correct proportion of starting materials and thus obtained a predetermined and specific proportion by weight of components (i), (ii), (iii) and (iv) and a predetermined and specific degree of alkoxylation.

The component of formula (iv) is preferably produced from one of the fats or oils used, preferably, in the first method of the present invention and which have been previously stated.

Detergent Compositions

Another additional object of the present invention is the detergent compositions which contain the compositions of the invention (mixture of alkoxylated mono-, di-, and triglycerides and glycerine)

The composition of the present invention is used, preferably, as surfactant or co-surfactant in detergent compositions wherein, preferably, they are contained in quantities which range from 0.25 and 20% by weight, although more preferably between 0.5 and 8% by weight.

The detergent compounds of the present invention may, additionally, contain one or more of the following additives, depending on the objective of the detergent compound, without this being a limited list:

1. Anionic surfactants such as sodium alkyl ether sulfate, ammonium alkyl ether sulfate, triethanolamine alkyl ether sulfate, sodium alkyl sulfate, ammonium alkyl sulfate, triethanolamine alkyl sulfate, sodium alkyl sulfonate, sodium alkene sulfonate such as sodium alpha olefin sulfonate, sodium alkane sulfonate, sodium alkyl aryl sulfonate such as alkyl benzene sulfonate, sulfosuccinates, and sulfosuccinamates.

2. Fatty acids or soaps derived from natural or synthetic substances such as coconut, oleic, soy and tallow fatty acids.

3. Ethoxylated alcohols.

4. Fatty acid esters derived from natural or synthetic substances such as glycol, ethylene glycol, diethylene glycol, propylene glycol, dipropylene glycol, sucrose, glucose or polyglycerine.

5. Ethoxylated esters of fatty acids such as hydroxy-type fatty acids.

6. Amphoteric surfactants such as alkyl amidopropyl betaine, alkyl betaine, alkyl amidopropyl sulfobetaine, alkyl sulfobetaine, cocoamphoacetates and cocoamphodiacetates.

7. Amine oxides such as dimethyl alkylamine oxides or alkyl amidopropylamine oxides.

8. Amides such as monoethanolamides, diethanolamides, ethoxylated amides or alkyl isopropanol amides.

9. Alkylpolyglycosides.

10. Alcohol ether carboxylates, ethoxylated fatty alcohols.

11. Cationic surfactants such as alkyl benzyl dimethyl ammonium halides, alkyl trimethyl ammonium halides, quaternized ethoxylated amines, esterquats derived from triethanolamine, methyldiethanolamine, dimethylamine propanediol and oligomers of said esterquats.

12. Additives to improve said formulations such as thickeners, pearling agents, opacifiers, antioxidants, preservatives, colouring agents or perfumes.

Particularly preferred are detergent compositions for washing fabrics, for manual dishwashing, for washing the hair or for personal hygiene, which contain the compositions according to the present invention, particularly detergent compositions for manual dishwashing.

The use of said compositions as surfactant or co-surfactant in detergent compositions also forms part of the object of the invention, particularly in detergent compositions for washing fabrics, for manual dishwashing, for washing the hair or for personal hygiene.

The use of said compositions as amplifying or promoting agents of foaming in detergent compositions also forms part of the object of the invention, particularly in detergent compositions for washing fabrics, for manual dishwashing, for washing the hair or for personal hygiene.

The following examples are given for the purposes of providing a person skilled in the art with a sufficiently clear and complete explanation of the present invention, but they should not be considered as limitations to the essential aspects of the object thereof, as has been stated in the previous paragraphs of this description.

EXAMPLES

Example 1

Preparation of Mixtures of Alkoxylated Mono-, Di-, and Triglycerides and Glycerine The mixtures of alkoxylated mono-, di-, and triglycerides and glycerine of Table 1 were prepared in accordance with the procedure described in the examples of patent application EP-A-1045021.

TABLE 1

Mixtures of alkoxylated mono-, di-, and triglycerides and glycerine (percentages by weight)

| | A | B | C1 | C2 | C3 | C4 | C5 |
|---|---|---|---|---|---|---|---|
| Chain (R) derived from . . . acid | Caprylic/ Capric | 2-ethyl hexanoic | coconut | coconut | coconut | palm | Caprylic/ Capric |
| Mono- | 78.3 | 85.5 | 59.9 | 70.2 | 77.3 | 74.5 | 52.7 |
| Di- | 20.0 | 13.8 | 34.0 | 26.8 | 20.9 | 23.4 | 38.3 |
| Tri- | 1.6 | 0.7 | 6.1 | 3.0 | 1.8 | 2.1 | 9.0 |
| ((i) + (ii) + (iii))/(iv) | 1.1 | 0.6 | 3.2 | 2.3 | 1.2 | 1.9 | 4.4 |
| m + n + l | 6.0 | 8.0 | 7.1 | 1.9 | 6.0 | 2.2 | 7.7 |

Mixtures A and B are in accordance with the invention, whilst mixtures C1-C5 are comparative examples.

Example 2

Dishwashing Composition Including a Single Type of Non-Ionic Surfactant

The dishwashing compositions of Table 3 were prepared, as indicated in Table 2.

TABLE 2

Dishwashing composition including a non-ionic surfactant (percentages by weight, which represent 100% of active material for each component)

| Components | % by weight |
|---|---|
| Sodium lauryl ether sulfate[1] | 13.5 |
| Amine oxide[2] | 3.0 |
| Non-ionic surfactant[3] | 3.5 |
| Demineralized water | Up to 100% |

[1]EMAL ® 270E (70% of active material with an average degree of ethoxylation of 2) marketed by Kao Chemicals Europe
[2]OXIDET ® DMCL-D (coconut-alkyldimethylamine oxide, 30% of active material) marketed by Kao Chemicals Europe
[3]As described in Table 3

The evaluation of the different compositions was carried out from the determination of the foaming power in the presence of grease (olive oil), according to the following procedure.

The foam volume of an aqueous solution of the product to be tested was determined at a concentration of 0.4 g/L (active product), at a water hardness of 20° HF (French degrees) and at a temperature of 40° C.

The measurements were carried out using a "SITA Foam Tester R-2000" stirrer (supplied by SITA Messtechnik GmbH), working at 1500 rpm, in stirring cycles of 10 seconds.

The foam volume was measured between each stirring cycle and 50 μL of grease (olive oil) were added.

When the foam volume (y-axis) is represented against the number of oil additions (x-axis), a parabolic-type curve is obtained, with a maximum for the foam value.

To compare the behaviour of the different products, the following curve parameters are taken into consideration:

Maximum foam volume: maximum point of the curve

Number of theoretical plates: cut with x-axis (number of oil additions) which corresponds to a foam volume of 100 mL The results of the evaluation are shown in Table 3.

TABLE 3

| Evaluation of the dishwashing compositions | | | |
|---|---|---|---|
| Dishwashing compositions | Non-ionic surfactant | Maximum volume foam (mL) | Number of theoretical plates |
| A | Mixture A (Example 1) | 766 | 50 |
| B | Mixture B (Example 1) | 782 | 58 |
| C1 | Mixture C1 (Example 1) | 521 | 40 |
| C2 | Mixture C2 (Example 1) | 382 | 39 |
| C3 | Mixture C3 (Example 1) | 511 | 44 |
| C4 | Mixture C4 (Example 1) | 408 | 38 |
| C5 | Mixture C5 (Example 1) | 424 | 43 |
| C6 | Ethoxylated alcohol $C_9$-$C_{11}$[1] | 468 | 39 |
| C7 | Alkyl polyglucoside[2] | 610 | 46 |

[1]NEODOL ® 91-9 (ethoxylated alcohol $C_9$-$C_{11}$ with an average degree of ethoxylation of 9) from Shell Chemicals

[1]PLANTAREN ® 2000 (Decyl polyglucoside) from Cognis Iberia SL/Cognis Deutschland GmbH & Co. KG The dishwashing compositions prepared in accordance with the invention (A-B) have a maximum foam volume and number of theoretical plates higher than that of the dishwashing compositions prepared with the comparative examples (C1-C7).

Example 3

Dishwashing Composition Including Additional Non-Ionic Surfactants

The dishwashing compositions were prepared as indicated in Table 4.

TABLE 4

| Dishwashing composition including two types of non-ionic surfactants (percentages by weight, which represent 100% of active material for each component) | | | | |
|---|---|---|---|---|
| | Dishwashing compositions | | | |
| Components | C | D | C8 | C9 |
| Sodium lauryl ether sulfate[1] | 13.5 | 13.5 | 13.5 | 13.5 |
| Amine oxide[2] | 3.0 | 3.0 | 3.0 | 3.0 |
| Mixture A (Example 1) | 3.5 | 3.0 | — | — |
| Mixture C3 (Example 1) | — | — | 3.5 | 3.0 |
| Branched ethoxylated alcohols C8[3] | — | 0.5 | — | 0.5 |
| Demineralized water | Up to 100% | Up to 100% | Up to 100% | Up to 100% |

[1]EMAL ® 270E (70% of active material with an average degree of ethoxylation of 2) marketed by Kao Chemicals Europe

[2]OXIDET ® DMCL-D (coconut-alkyldimethylamine oxide, 30% of active material) marketed by Kao Chemicals Europe

[3]FINDET ® HEX-16 (2-ethylhexanol and average degree of ethoxylation of 4) produced by Kao Chemicals Europe

TABLE 5

| Evaluation of the dishwashing compositions | | |
|---|---|---|
| Dishwashing composition | Maximum foam volume (mL) | Number of theoretical plates |
| C | 766 | 50 |
| D | 863 | 55 |
| C8 | 511 | 44 |
| C9 | 635 | 47 |

From the experimental results it can be concluded that the fact of adding a second type of non-ionic surfactant (of the branched alcohol type with 8 carbon atoms and with an average degree of propoxylation of 4) causes an increase in the maximum foam volume and the number of theoretical plates, both in the dishwashing compositions which include the compositions in accordance with the invention (C and D) as well as in the dishwashing compositions which include the comparative examples (C8 and C9).

Despite the increases observed in the comparative examples, the maximum foam volume and the number of theoretical plates continues to be considerably lower than the results obtained by the dishwashing composition that only includes the composition of alkoxylated mono-, di-, and triglycerides and glycerine in accordance with the invention.

The invention claimed is:

1. A composition which comprises:

(i) at least one component represented by formula (1), wherein, independently, one of the symbols B1, B2, B3 represents an acyl group represented by —CO—R and the remaining ones represent H;

(ii) at least one component represented by formula (1), wherein, independently, two of the symbols B1, B2 and B3 represent an acyl group represented by —CO—R and the remaining one represents H;

(iii) at least one component represented by formula (1), wherein, independently, each one of the symbols B1, B2 and B3 represents an acyl group represented by —CO—R; and (iv) at least one component represented by formula (1), wherein each one of B1, B2 and B3 represents H, (1)

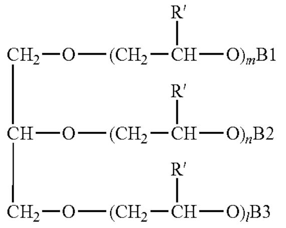

with the proportion by weight of components (i)/(ii)/(iii) of 60-90/10-35/less than 10, wherein R' represents H or $CH_3$, and each one of m, n, or l represents, independently, a number from 0 to less than 9, the sum of m, n and l being in the range of over 5 and less than 9, wherein in the acyl group represented by —CO—R, R represents an alkyl or alkenyl group, linear or branched, of 6 to 9 carbon atoms, and wherein the proportion by weight (i)+(ii)+(iii)/(iv) is in the range of 2.0:0.5 to 0.5:3.

2. The composition in accordance with claim 1, characterized in that the proportion by weight (i)+(ii)+(iii)/(iv) is in the range of 1.5:0.8 to 0.8:2.5.

3. The composition in accordance with claim 1, characterized in that R' represents H.

4. A process for preparing a composition in accordance with claim 1, which comprises the following stages:

a) subjecting a mixture of glycerine and a component of formula (2) to an interesterification reaction:

wherein R represents an alkyl or alkenyl group, linear or branched, of 6 to 9 carbon atoms,

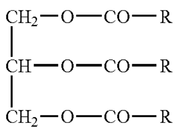

(2)

and b) subjecting the reaction mixture produced in stage a) to an alkoxylation using an alkylene oxide with 2 or 3 carbon atoms in the presence of an alkaline catalyst.

5. A process for preparing a composition in accordance with claim 1, which comprises the following stages:

a') reacting a mixture of glycerine with alkylene oxide of 2 or 3 carbon atoms in the presence of an alkaline catalyst, and b') reacting the reaction mixture produced in stage a') with a component of formula (3)

R—CO—OX (3)

wherein R represents an alkyl or alkenyl group, linear or branched, of 6 to 9 carbon atoms and X represents a methyl group or H.

6. A detergent composition which contains a composition according to claim 1, in a quantity of 0.25 to 20% by weight.

7. The detergent composition according to claim 6, wherein the composition is contained in a quantity of 0.5 to 8% by weight.

8. The detergent composition according to claim 6, characterized in that said detergent compound is a detergent compound for washing fabrics, for manual dishwashing, for washing the hair or for personal hygiene.

9. A method of washing a material comprising contacting the material with a composition as defined in claim 1.

10. The method according to claim 9, wherein washing a material is washing fabrics, manual dishwashing, washing the hair or personal hygiene.

11. A method of amplifying or promoting foaming in a detergent composition comprising admixing the detergent composition with a composition as defined in claim 1.

12. The method according to claim 11, wherein the detergent composition is a detergent composition for washing fabrics, for manual dishwashing, for washing the hair or for personal hygiene.

13. The composition in accordance with claim 2, characterized in that R' represents H.

14. A detergent composition which contains a composition according to claim 2, in a quantity of 0.25 to 20% by weight.

15. A detergent composition which contains a composition according to claim 3, in a quantity of 0.25 to 20% by weight.

16. The detergent composition according to claim 14, wherein the composition is contained in a quantity of 0.5 to 8% by weight.

17. The detergent composition according to claim 15, wherein the composition is contained in a quantity of 0.5 to 8% by weight.

18. The detergent composition according to claim 7, characterized in that said detergent compound is a detergent compound for washing fabrics, for manual dishwashing, for washing the hair or for personal hygiene.

* * * * *